United States Patent [19]

Tsutsumi et al.

[11] Patent Number: 4,971,957

[45] Date of Patent: Nov. 20, 1990

[54] CARBOXAMIDE COMPOUNDS, PROCESSES FOR PREPARING THE SAME AND A PHARMACEUTICAL COMPOSITION CONTAINING THE SAME

[75] Inventors: Kazuhiko Tsutsumi, Tokushima; Eiji Uesaka, Naruto; Kayoko Shinomiya, Tokushima; Yoshihiko Tsuda, Naruto; Yauso Shoji; Atsushi Shima, both of Tokushima, all of Japan

[73] Assignee: Otsuka Pharmaceutical Factory, Inc., Tokushima, Japan

[21] Appl. No.: 373,837

[22] Filed: Jun. 29, 1989

[30] Foreign Application Priority Data

Jun. 29, 1988 [JP] Japan ................................. 63-163082
Jun. 15, 1989 [JP] Japan ................................. 1-152784
Jun. 21, 1989 [JP] Japan ................................. 1-160171

[51] Int. Cl.$^5$ .......................... A01N 57/14; C07F 9/18
[52] U.S. Cl. ................................... 514/79; 514/80; 514/82; 514/85; 514/86; 514/89; 514/90; 514/91; 514/92; 514/94; 514/114; 514/119; 544/32; 544/39; 544/105; 544/232; 544/243; 544/244; 546/22; 546/23; 548/112; 548/113; 558/154; 558/190; 558/196; 558/197; 558/198

[58] Field of Search ............... 558/140, 154, 196, 197, 558/198; 564/15; 544/32, 39, 105, 232, 244, 243; 546/22, 23; 548/112, 113; 514/119, 79, 80, 82, 85, 86, 89, 90, 91, 92, 94, 114

[56] References Cited

U.S. PATENT DOCUMENTS 4,822,780  4/1989  Tsuda et al. ........................ 514/119

FOREIGN PATENT DOCUMENTS 0273444  7/1988  European Pat. Off. .
61-151199  7/1986  Japan .

*Primary Examiner*—Richard L. Raymond
*Assistant Examiner*—Raymond Covington
*Attorney, Agent, or Firm*—Sughrue, Mion, Zinn, Macpeak & Seas

[57] ABSTRACT

Novel carboxamide compounds represented by the general formula (I) possess excellent activities for lowering lipids and thus they are useful as agents for treating and preventing various diseases (hyperlipidemia) such as hypercholesterolemia, hypertriglyceridemia, hyperphospholipidemia, hyperlipacidemia, and the like.

5 Claims, No Drawings

CARBOXAMIDE COMPOUNDS, PROCESSES FOR PREPARING THE SAME AND A PHARMACEUTICAL COMPOSITION CONTAINING THE SAME

FIELD OF THE INVENTION

The present invention relates to novel carboxamide compounds. More particularly, the invention relates to said carboxamide compounds, processes for preparing the same and a pharmaceutical composition for treating hyperlipidemia containing, as the active ingredient, said carboxamide compound.

PRIOR ART

The carboxamide compounds of the present invention are novel compounds which have not been known from any of prior art literatures.

SUMMARY OF THE INVENTION

An object of the present invention is to provide novel carboxamide compounds.

Another object of the invention is to provide processes for preparing said novel carboxamide compounds.

Further object of the present invention is to provide a pharmaceutical composition for treating and/or preventing hyperlipidemia containing, as the active ingredient, said carboxamide compound.

DETAILED EXPLANATION OF THE INVENTION

According to the present invention, it is provided that novel carboxamide compounds represented by the general formula (I),

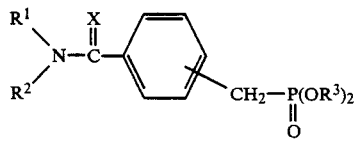

wherein
$R^1$ and $R^2$ are each:
 a hydrogen atom;
 a lower alkyl group;
 a phenyl group which may have 1 to 3 substituents selected from the group consisting of a halogen atom, a carbamoyl group, an N-(lower alkyl)carbamoyl group, an N-(cycloalkyl)carbamoyl group, an N-(phenyl)carbamoyl group which may have halogen atoms, lower alkoxy groups or lower alkyl groups as substituents in the phenyl ring, an N-(phenyl-lower alkyl)carbamoyl group, a lower alkanoyl group, a benzoyl group, an N,N-di(lower alkyl)amino group, a phenylthio group, a lower alkylthio group, a lower alkylsulfinyl group, a phenylsulfinyl group, a 4-phenylpiperazinylcarbonyl group, a 4-(phenyl-lower alkyl)piperazinylcarbonyl group, a piperidinylcarbonyl group and a sulfamoyl group;
 a lower alkoxycarbonyl-lower alkyl group;
 a pyridyl group which may have 1 to 3 substituents selected from the group consisting of a halogen atom, a lower alkoxy group and a lower alkoxycarbonyl group;
 an N-phenylamino group;
 a naphthyl group which may have halogen atoms as substituents;
 a pyrimidinyl group;
 an isoxazolyl group which may have lower alkyl groups as substituents; or
 an N-phthalazinylamino group;
further, $R^1$ and $R^2$ together with the adjacent nitrogen atom being bonded thereto form a heterocyclic group consisting of an indolin-1-yl group, a 1,2,3,4-tetrahydroquinolin-1-yl group which may have halogen aotms as substituents, a 1,2,3,4-tetrahydroisoquinolin-2-yl group, a 2,3-dihydro-4H-1,4-benzoxazin-4-yl group which may have a phenyl group at 2- or 3-position in the benzoxazine ring, and a phenothiazin-10-yl group which may have halogen atoms as substituents in the benzene ring;
provided that, $R^1$ and $R^2$ should not be hydrogen atoms at the same time;
and when any one of $R^1$ and $R^2$ is a lower alkyl group, then another one is a phenyl group having a halogen atom and a benzoyl group at the same time as substituents; or when any one of $R^1$ and $R^2$ is a phenyl group having a halogen atom as substituent, then another one is a lower alkoxycarbonyl-lower alkyl group;
further when any one of $R^1$ and $R^2$ is a phenyl group, then another one is an N-phenylamino group;
$R^3$ is a lower alkyl group; and
X is an oxygen atom or a sulfur atom.

In the above-mentioned general formula (I), the substituents defined in the symbols $R^1$, $R^2$ and $R^3$ are exemplified as follows.

As to the lower alkyl group, a $C_{1-6}$ alkyl group such as methyl, ethyl, propyl, isopropyl, butyl, t-butyl, pentyl and hexyl groups can be exemplified.

As to the cycloalkyl group, a $C_{3-8}$ cycloalkyl group such as cyclopropyl, cyclobutyl, cyclopentyl, cyclohexyl, cycloheptyl and cyclooctyl groups can be exemplified.

As to the lower alkoxy group, a $C_{1-6}$ alkoxy group such as methoxy, ethoxy, propoxy, butoxy, t-butoxy, pentyloxy and hexyloxy groups can be exemplified.

As to the phenyl-lower alkyl group, a phenyl($C_{1-6}$ alkyl) group such as benzyl, α-phenethyl, β-phenethyl, 3-phenylpropyl, 4-phenylbutyl, 1,1-dimethyl-2-phenylethyl, 5-phenylpentyl and 6-phenylhexyl groups can be exemplified.

As to the N-(lower alkyl)carbamoyl group, an N-($C_{1-6}$ alkyl)carbamoyl group such as N-methylcarbamoyl, N-ethylcarbamoyl, N-propylcarbamoyl, N-butylcarbamoyl, N-(t-butyl)carbamoyl, N-pentylcarbamoyl and N-hexylcarbamoyl groups can be exemplified.

As to the N-(cycloalkyl)carbamoyl group, an N-($C_{3-8}$ cycloalkyl)carbamoyl group such as N-cyclopropylcarbamoyl, N-cyclobutylcarbamoyl, N-cyclopentylcarbamoyl, N-cyclohexylcarbamoyl, N-cycloheptylcarbamoyl and N-cyclooctylcarbamoyl groups can be exemplified.

As to the N-(phenyl)carbamoyl group which may have halogen atoms, lower alkoxy groups or lower alkyl groups as substituents in the phenyl ring, phenylcarbamoyl, N-(o-chlorophenyl)carbamoyl, N-(m-chlorophenyl)carbamoyl, N-(p-chlorophenyl)carbamoyl, N-(p-bromophenyl)carbamoyl, N-(p-fluorophenyl)carbamoyl, N-(o-methoxyphenyl)carbamoyl, N-(m-methoxyphenyl)carbamoyl, N-(p-methoxyphenyl)carbamoyl, N-(o-ethoxyphenyl) carbamoyl, N-(m-propoxyphenyl)carbamoyl, N-(p-butoxyphenyl)carbamoyl, N-(o-pentyloxyphenyl)carbamoyl, N-(m-hexyloxyphenyl)carbamoyl, N-(o-methylphenyl)carbamoyl, N-(m-methylphenyl)carbamoyl, N-(p-methylphenyl)carbamoyl, N-(p-ethylphenyl)carbamoyl, N-(m-propylphenyl)carbamoyl, N-(p-butylphenyl)carbamoyl, N-(p-pentylphenyl)carbamoyl and N-(p-hexylphenyl)carbamoyl groups can be exemplified.

As to the N-(phenyl-lower alkyl)carbamoyl group, an N-(phenyl-$C_{1-6}$ alkyl)carbamoyl group such as N-(benzyl)carbamoyl, N-(α-phenethyl)carbamoyl, N-(β-phenethyl)carbamoyl, N-(3-phenylpropyl)carbamoyl, N-(4-phenylbutyl)carbamoyl, N-(1,1-dimethyl-2-phenylethyl)carbamoyl, N-(5-phenylpentyl)carbamoyl and N-(6-phenylhexyl)carbamoyl groups can be exemplified.

As to the lower alkanoyl group, a $C_{1-6}$ alkanoyl group such as acetyl, propionyl, butyryl, isobutyryl, valeryl, isovaleryl, pivaloyl and hexanoyl groups can be exemplified.

As to the lower alkoxycarbonyl group, a $C_{1-6}$ alkoxycarbonyl group such as methoxycarbonyl, ethoxycarbonyl, propoxycarbonyl, isopropoxycarbonyl, butoxycarbonyl, pentyloxycarbonyl and hexyloxycarbonyl groups can be exemplified.

As to the halogen atom, fluorine atom, chlorine atom, bromine atom and iodine atom can be exemplified.

As to the N,N-di(loweralkyl)amino group, an N,N-di($C_{1-6}$ alkyl)amino group such as N,N-dimethylamino, N,N-diethylamino, N,N-dipropylamino, N,N-dihexylamino, N-methyl-N-ethylamino, N-methyl-N-butylamino and N-ethyl-N-hexylamino groups can be exemplified.

As to the lower alkylsulfinyl group, a $C_{1-6}$ alkylsulfinyl group such as methylsulfinyl, ethylsulfinyl, propylsulfinyl, butylsulfinyl, pentylsulfinyl and hexylsulfinyl groups can be exemplified.

As to the phenylpiperazinylcarbonyl group, 2-phenylpiperazinylcarbonyl, 3-phenylpiperazinylcarbonyl and 4-phenylpiperazinylcarbonyl groups can be exemplified.

As to the (phenyl-lower alkyl)piperazinylcarbonyl group, a (phenyl-$C_{1-6}$ alkyl)piperazinylcarbonyl group such as 2-(benzyl)piperazinylcarbonyl, 3-(benzyl)piperazinylcarbonyl, 4-(benzyl)piperazinylcarbonyl, 4-(α-phenethyl)piperazinylcarbonyl, 4-(β-phenethyl)piperazinylcarbonyl, 4-(4-phenylbutyl)piperazinylcarbonyl and 4-(6-phenylhexyl)piperazinylcarbonyl groups can be exemplified.

As to the lower alkoxycarbonyl-lower alkyl group, a $C_{1-6}$ alkoxycarbonyl-$C_{1-6}$ alkyl group such as methoxycarbonylmethyl, ethoxycarbonylmethyl, 2-(ethoxycarbonyl)ethyl, 3-(ethoxycarbonyl)propyl, 4-(ethoxycarbonyl)butyl, 5-(ethoxycarbonyl)pentyl, 6-(ethoxycarbonyl)hexyl, 2-(4-butoxycarbonyl)ethyl and (6-hexyloxycarbonyl)methyl groups can be exemplified.

As to the naphthyl group which may have halogen atoms as substituents, α-naphthyl, β-naphthyl, 2-chloro-1-naphthyl, 1-chloro-2-naphthyl, 4-chloro-1-naphthyl, 5-chloro-1-naphthyl, 7-chloro-1-naphthyl, 2-bromo-1-naphthyl, 4-bromo-2-naphthyl, 8-bromo-2-naphthyl and 4-fluoro-1-naphthyl groups can be exemplified.

As to the pyrimidinyl group, 2-pyrimidinyl, 4-pyrimidinyl, 5-pyrimidinyl and 6-pyrimidinyl groups are involved.

As to the N-phthalazinylamino group, N-(1-phthalazinyl)amino, N-(5-phthalazinyl)amino and N-(6-phthalazinyl)amino groups are involved.

As to the 1,2,3,4-tetrahydroquinolin-1-yl which may have halogen atoms as substituents, 1,2,3,4-tetrahydroquinolin-1-yl, 2-chloro-1,2,3,4-tetrahydroquinolin-1-yl, 3-chloro-1,2,3,4-tetrahydroquinolin-1-yl, 4-chloro-1,2,3,4-tetrahydroquinolin-1-yl, 5-chloro-1,2,3,4-tetrahydroquinolin-1-yl, 6-chloro-1,2,3,4-tetrahydroquinolin-1-yl, 7-chloro-1,2,3,4-tetrahydroquinoline-1-yl, 8-chloro-1,2,3,4-tetra-hydroquinolin-1-yl, 3-bromo-1,2,3,4-tetrahydroquinolin-1-yl, 4-bromo-1,2,3,4-tetrahydroquinolin-1-yl, 5-bromo-1,2,3,4-tetrahydroquinolin-1-yl, 6-bromo-1,2,3,4-tetrahydroquinolin-1-yl, 7-bromo-1,2,3,4-tetrahydroquinolin-1-yl, 8-bromo-1,2,3,4-tetrahydroquinolin-1-yl, 5-fluoro-1,2,3,4-tetrahydroquinolin-1-yl and 8-fluoro-1,2,3,4-tetrahydroquinolin-1-yl groups can be exemplified.

As to the isoxazolyl group which may have lower alkyl groups as substituents, 3-isoxazolyl, 4-isoxazolyl, 5-isoxazolyl, 5-methyl-3-isoxazolyl, 5-methyl-4-isoxazolyl, 5-propyl-3-isoxazolyl, 4-hexyl-3-isoxazolyl, 4-methyl-3-isoxazolyl and 4-ethyl-5-isoxazolyl groups cane be exemplified.

As to the phenyl group which may have 1 to 3 substituents selected from the group consisting of a halogen atom; a carbamoyl group, an N-(lower alkyl)carbamoyl group; an N-(cycloalkyl)carbamoyl group; an N-(phenyl)carbamoyl group which may have halogen atoms, lower alkoxy groups or lower alkyl groups as substituents in the phenyl ring; an N-(phenyl-lower alkyl)carbamoyl group; a lower alkanoyl group; a benzoyl group; an N,N-di(lower alkyl)amino group; a phenylthio group; a lower alkylthio group; a lower alkylsulfinyl group; a phenylsulfinyl group; a 4-phenylpiperazinylcarbonyl group; a 4-(phenyl-lower alkyl)piperazinylcarbonyl group; a piperidinylcarbonyl group and a sulfamoyl group, there can be exemplified phenyl group and 4-bromo-2-carbamoylphenyl, 4-chloro-3-carbamoylphenyl, 3-bromo-5-carbamoylphenyl, 3,4-dibromo-5-carbamoylphenyl, 4-chloro-2-(N-methylcarbamoyl)phenyl, 5-chloro-2-(N-methylcarbamoyl)phenyl, 6-chloro-2-(N-methylcarbamoyl)phenyl, 4-bromo-2-(N-methylcarbamoyl)phenyl, 6-bromo-2-(N-methylcarbamoyl)phenyl, 4-chloro-2-(N-cyclohexylcarbamoyl)phenyl, 4-bromo-2-(N-cyclohexylcarbamoyl)phenyl, 6-bromo-2-(N-cyclohexylcarbamoyl)phenyl, 4-chloro-2-{N-(p-chlorophenyl)carbamoyl}phenyl, 4-bromo-2-{N-(p-chlorophenyl)carbamoyl}phenyl, 4-chloro-2-{N-(o-methoxyphenyl)carbamoyl}phenyl, 4-bromo-2-(N-(o-methoxyphenyl)carbamoyl}phenyl, 4-chloro-2-(N-(p-methoxyphenyl)carbamoyl]phenyl, 4-chloro-2{N-(p-methylphenyl)carbamoyl}phenyl, 4-bromo-2-(N-(p-methylphenyl)carbamoyl]phenyl, 4-bromo-2-N-(o-methylphenyl)carbamoyl]phenyl, 4-chloro-2-(N-benzylcarbamoyl)phenyl, 4-bromo-2-(N-benzylcarbamoyl)phenyl, 4-bromo-2-[N-(o-phenethyl)carbamoyl]phenyl, 4-bromo-2-(N-(o-phenethyl)carbamoyl phenyl, 3-bromo-4-chloro-5-carbamoylphenyl, 4-bromo-2-acetylphenyl, 3-bromo-2-acetylphenyl, 4-chloro-2-propionylphenyl, 2-bromo-4-valerylphenyl, 2-bromo-4-acetylphenyl, 2-chloro-5-acetylphenyl, 4-bromo-2-benzoylphenyl, 5-bromo-3-benzoylphenyl, 4-bromo-2,6-dibenzoylphenyl, 4-chloro-5-bromo-2-benzoylphenyl, 2-dimethylaminophenyl, 3-dimethylaminophenyl, 4-dimethylaminophenyl, 2-(phenylthio)phenyl, 3-(phenylthio)phenyl, 4-(phenylthio)phenyl, 2,3-dibromo-4-(phenylthio)phenyl, 2-(methylthio)phenyl, 3-(methylthio)phenyl, 4-(methylthio)phenyl, 4-(butylthio)phenyl, 2-methylsulfinylphenyl, 4-methylsulfinylphenyl, 3- phenylsulfinylphenyl, 4-phenylsulfinylphenyl, 4-chloro-2-(4-phenylpiperazinylcarbonyl)phenyl, 4-bromo-2-(4-phenylpiperazinylcarbonyl)phenyl, 4-chloro-2-(4-benzylpiperazinylcarbonyl)phenyl, 4-bromo-2-(4-benzylpiperazinylcarbonyl)phenyl, 4-chloro-2-(piperidinylcarbonyl)phenyl, 4-bromo-2-(piperidinylcarbonyl)phenyl, 2-sulfamoylphenyl, 3-sulfamoylphenyl, 4-sulfamoylphenyl, 2-benzoylphenyl, 3-benzoylphenyl, 4-benzoylphenyl, 2-acetylphenyl, 3-acetylphenyl, 4-acetylphenyl, 4-propionylphenyl, 3-valerylphenyl, 4-chloro-2-benzoylphenyl, 3-chloro-2-benzoylphenyl and 3-chloro-5-benzoylphenyl groups can be exemplified.

As to the pyridyl group which may have 1 to 3 substituents selected from the group consisting of a halogen atom, a lower alkoxy groups and a lower alkoxycarbonyl group, there can be exemplified 2-pyridyl, 3-pyridyl, 4-pyridyl, 6-chloro-2-pyridyl, 5-chloro-2-pyridyl, 3-bromo-4-pyridyl, 5-bromo-2-pyridyl, 3-iodo-2-pyridyl, 4-fluoro-2-pyridyl, 2,6-dibromo-3-pyridyl, 2-chloro-3-bromo-4-pyridyl, 2,4,6-tribromo-3-pyridyl, 2-methoxy-5-pyridyl, 3-methoxy-5-pyridyl, 4-methoxy-5-pyridyl, 2-methoxy-4-pyridyl, 2-ethoxy-5-pyridyl, 4-butoxy-5-pyridyl, 2-hexyloxy-5-pyridyl, 5-methoxycarbonyl-2-pyridyl, 5-methoxycarbonyl-3-pyridyl, 5-ethoxycarbonyl-2-pyridyl and 5-penthyloxycarbonyl-2-pyridyl groups can be exemplified.

Carboxamide compounds represented by the general formula (I) possess excellent activities for lowering lipids and thus they are useful as agents for treating hyperlipidemia, and are effective for treating and preventing various diseases (hyperlipidemia) such as hypercholesterolemia, hypertriglyceridemia, hyperphospholipidemia, hyperlipacidemia, and the like.

Next, processes for preparing carboxamide compounds of the present invention will be explained in detail as follows, thus carboxamide compounds represented by the general formula (I) can be prepared by various methods, in which typical methods are shown in the following Reaction Scheme 1-5.

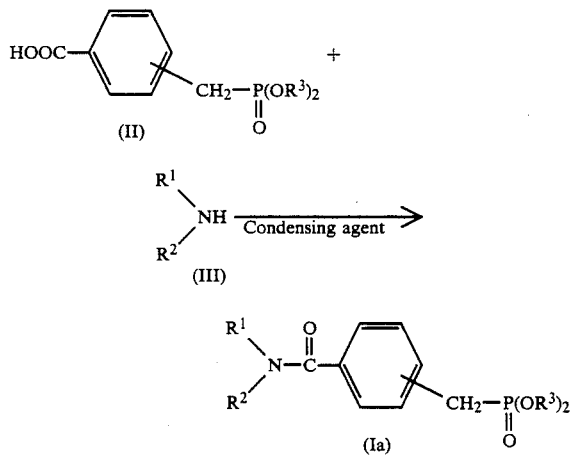

In the above-mentioned Reaction Scheme—1, $R^1$, $R^2$ and $R^3$ are the same as defined previously.

According to the Reaction Scheme—1, a carboxamide compound (Ia) of the present invention can be prepared by condensing a carboxylic acid derivative (II) with an amine (III). The above-mentioned condensation is carried out, in a suitable solvent, in the presence of a condensing agent.

As to the condensing agent to be used in the reaction, any known condensing agent used in usual condensation reactions can also be used, and the examples are included N,N-dicyclohexylcarbodiimide, 1-hydroxybenzotriazole, N-hydroxysuccinimide, diethyl phosphorocyanidate, diphenylphosphoryl azide and the like. Particularly, diethyl phosphorocyanidate is preferably used together with triethylamine. Furthermore, as to the solvent to be used in the reaction, any aprotic solvent known in the prior art can be used, particularly N,N-dimethylformamide (DMF) is used preferably.

In the reaction, the ratio of the amount of a carboxylic acid derivative (II) to the amount of an amine (III) is not specifically restricted and can be selected from wide range, and generally an equimolar to excess quantity, preferably an equimolar quantity of the latter may be used to the former. Furthermore, an equimolar to excess quantity, preferably slightly excess quantity of the condensing agent may be used to the carboxylic acid derivative (II). As to the reaction temperature, an ice-cooling to an ambient temperature condition may be employed, and generally the reaction is completed in about 0.5 to 2 hours.

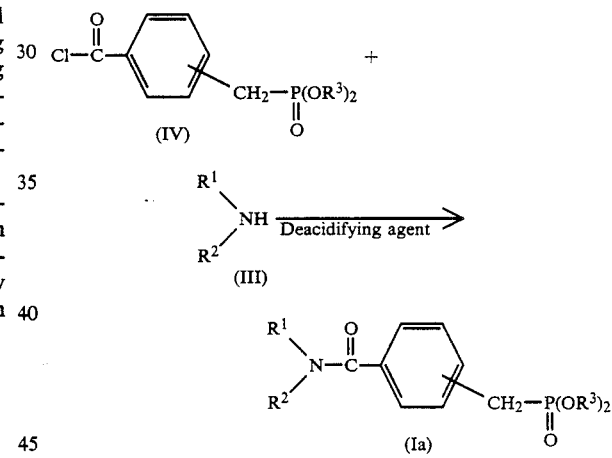

In the above-mentioned Reaction Scheme—2, $R^1$, $R^2$ and $R^3$ are the same as defined previously.

According to the Reaction Scheme—2, a carboxamide compound (Ia) of the present invention can be prepared by reacting a carboxylic acid chloride derivative (IV) with an amine (III).

The reaction is generally carried out in a suitable solvent, in the presence of a deacidifying agent. As to the deacidifying agent, any known deacidifying agent which will not give any adverse effect to the reaction may be used, and the examples are preferably included tertiary amines such as triethylamine, diethylaniline, N-methylmorpholine, pyridine, 4-dimethylaminopyridine and the like. As to the solvent, the examples are included aromatic and aliphatic hydrocarbons such as benzene, toluene, xylene, petroleum ether and the like; acyclic- and cyclic-ethers such as diethyl ether, dimethoxyethane, tetrahydrofuran (THF), 1,4-dioxane and the like; ketones such as acetone, methyl ethyl ketone, acetophenone and the like; halogenated hydrocarbons such as dichloromethane, chloroform, carbon tetrachloride, 1,2-dichloroethane and the like.

In the reaction, the ratio of the amount of a carboxylic acid chloride (IV) to the amount of an amine (III) is not specifically restricted and can be selected from a wide range, and generally an equimolar to excess quantity of the former may be used to the latter. Furthermore, generally an equimolar to slightly excess quantity of the above-mentioned deacidifying agent may preferably be used to the carboxylic acid chloride derivative (IV). The reaction may be proceeded either at room temperature or under cooling or under heating condition, and preferably at temperature condition within room temperature to the refluxing temperature of the solvent, and generally the reaction is completed in about 0.5 to 10 hours.

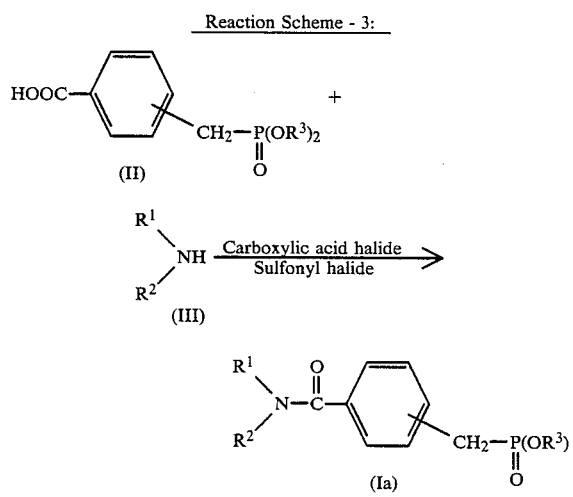

In the Reaction Scheme—3, $R^1$, $R^2$ and $R^3$ are the same as defined previously.

According to the Reaction Scheme—3, a carboxamide compound (Ia) of the present invention can be prepared by converting a carboxylic acid derivative (II) into a mixed acid anhydride, then mixed acid anhydride is reacted with an amine (III).

The conversion of a carboxylic acid derivative (II) into a carboxamide compound (Ia) is generally carried out in a suitable solvent, in the presence of a carboxylic acid halide or a sulfonyl halide which forms the desired mixed acid anhydride, together with a deacidifying agent. As to the carboxylic acid halide and sulfonyl halide to be used in the reaction, generally ethyl chlorocarbonate, isobutyl chlorocarbonate, p-toluenesulfonyl acid chloride, benzenesulfonyl acid chloride and the like can be involved. Among these acid hilide compounds, ethyl chlorocarbonate is preferably used. As to the deacidifying agent, any known agent which does not give any adverse effect to the reaction may be used, and the examples including tertiary amines such as triethylamine, diethylaniline, N-methylmorpholine, pyridine and the like. As to the solvent, aromatic and aliphatic hydrocarbons such as benzene, toluene, xylene, petroleum ether and the like; acyclic or cyclic ethers such as diethyl ether, dimethoxyethane, tetrahydrofuran (THF), 1,4-dioxane and the like; ketones such as acetone, methyl ethyl ketone, acetophenone and the like; and halogenated hydrocarbons such as dichloromethane, chloroform, carbon tetrachloride, 1,2-dichloroethane and the like can be exemplified.

In the reaction, the ratio of the amount of a carboxylic acid derivative (II) to the amount of an amine (III) is not specifically restricted and generally an equimolar to excess quantity of the latter may be used to the former. Furthermore, generally an equimolar to slightly excess quantities of the above-mentioned carboxylic acid halide and sulfonyl halide as well as deacidifying agent may preferably be used to the carboxylic acid derivative (II). The reaction may be proceeded either under cooling condition or at room temperature and under heating, and generally the reaction may preferably be carried under condition within room temperature to the refluxing temperature of the solvent, and generally the reaction is completed in about 0.5 to 5 hours.

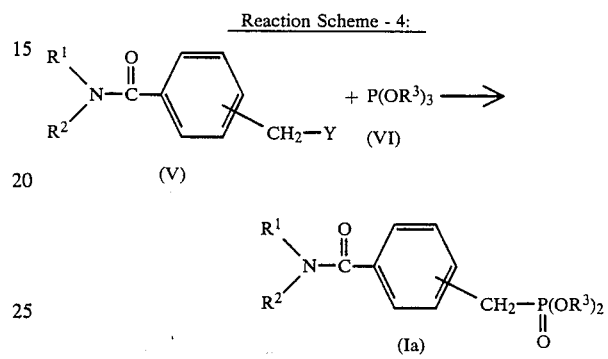

In the Reaction Scheme—4, $R^1$, $R^2$ and $R^3$ are the same as defined previously; and Y is a halogen atom.

According to the Reaction Scheme—4, a carboxamide compound (Ia) of the present invention can be prepared by reacting a haloamide derivative (V) with a phosphite (VI).

The reaction can be carried out in a solvent which does not give any adverse effect to the reaction, for example in a lower alcohol, an aromatic or aliphatic hydrocarbon, or N,N-dimethylformamide and the like, however, generally the reaction may preferably be carried out in the absence of a solvent.

In carrying out the reaction, the ratio of the amount of a haloamide derivative (V) to the amount of a, phosphite (VI) is that, generally an excess amount of the latter may be used to the former, and the reaction is generally carried out at 130°–180° C., preferably at about 140°–150° C., and the reaction time is depends on the type of phosphite (VI) to be used, and generally is about 0.5 to 3 hours.

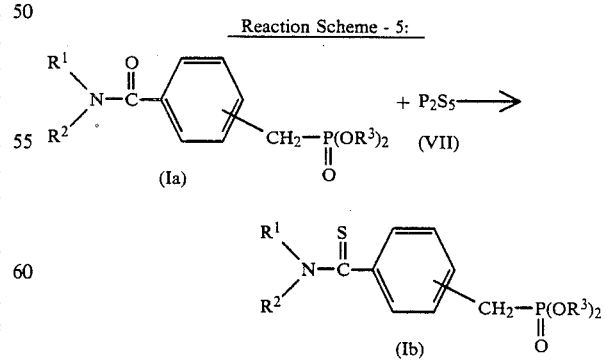

In the Reaction Scheme—5, $R^1$, $R^2$ and $R^3$ are the same as defined previously.

According to Reaction Scheme—5, a carboxamide compound (Ib) of the present invention can be prepared by reacting a carboxamide compound (Ia) with phosphorus pentasulfide (VII).

The carboxamide compound (Ia) to be used in the reaction is obtained by any one of methods shown by Reaction Schemes 1-4, and the reaction of said carboxamide compound (Ia) with phosphorus pentasulfide is carried out in a suitable solvent. As to the solvent, generally aprotic solvent, for example tertiary amine such as pyridine, triethylamine, dimethylaniline and the like; aromatic hydrocarbon such as benzene, toluene, xylene and the like; and acetonitrile and the like can advantageously be used. Among those solvents, a mixture of benzene with pyridine is preferably used, and its ratio of the former volume to the latter is generally about 4 to 5 times.

In the reaction, the ratio of the amount of a compound (Ia) to the amount of phosphorus pentasulfide (VII) is not specifically restricted and can be selected from a wide range, generally an equimolar to excess quantity, preferably about 1.5 to 2.5 times molar quantity of the latter may be used to the former. The reaction is generally carried out at room temperature to the refluxing temperature of the solvent, preferably at about 70° to 90° C., and generally the reaction is completed in about 2 to 10 hours.

The objective carboxamide compounds of the present invention obtained in the Reaction Schemes 1-5 can be isolated and purified by the conventional separation procedures, such as solvent extraction, distillation, recrystallization, column chromatography, preparative thin layer chromatography and the like.

The carboxamide compounds represented by the general formula (I) of the present invention can be used as the active ingredient to be contained in pharmaceutical composition for treating and preventing various diseases caused by hyperlipidemia, such as hypercholesterolemia, hypertriglyceridemia, hyperphospholipidemia, hyperlipacidemia and the like, on the basis of their excellent pharmacological activities, especially effects for lowering the concentration of lipids in blood, such as effects for lowering the concentrations of cholesterol, triglycerides, phospholipids, fatty acids and the like in blood. Furthermore, the carboxamide compounds represented by the general formula (I) of the present invention are also considerably effective for preventing and treating arteriosclerosis induced by the above-mentioned diseases caused by hyperlipidemia.

In addition to the above, the carboxamide compounds represented by the general formula (I) according to the present invention are characterized in their pharmacological activities which can be prolonged for a certain length of time, as well as they have lower toxicities, thus the carboximide compounds are quite suitable as the active ingredients for treating and preventing various diseases caused by hyperlipidemia.

The pharmaceutical composition for treating and preventing hyperlipidemia according to the present invention contains, as the essential factor, at least one carboxamide compounds represented by the general formula (I). Generally, said pharmaceutical composition is prepared in various forms of pharmaceutical preparations depend on methods of administration, by admixing the carboxamide compound with none toxic pharmaceutically acceptable carriers which are commonly used in pharmaceutical preparations, any pharmaceutical composition thus prepared is administered to a patient of hyperlipidemia and/or a patient of arteriosclerosis as for a treating agent, or administered as for a preventing these diseases.

As to the none toxic pharmaceutically acceptable carriers, which are commonly used depend on various preparation forms, any type of diluents or solvents, fillers, bulking agents, binding agents, dispersing agents, disintegrating agents, surface active agents, lubricants, excipients and wetting agents can be exemplified. Furthermore, if necessary, dissolving adjuvants, buffering agents, preservatives, coloring agents, perfumes, seasoning agents, and the like which are commonly used in pharmaceutical field may also be added to the pharmaceutical compositions.

Administration unit forms of pharmaceutical compositions according to the present invention are not specifically restricted and can be selected widely, depend on various therapeutic purposes, for example, oral administration preparations such as tablets, capsules, granules, pills, syrups, liquids, emulsions, suspensions and the like, parenteral administration preparations such as injection preparations (subcutaneously, intravenously, intramuscularly, intraperitoneally and the like) and suppositories. Among these preparations, oral administrations are particularly preferable.

The pharmaceutical compositions in the abovementioned various forms can be prepare by usual methods. For example, in preparing the oral administration preparations such as tablets, capsules, granules and pills, they can be prepared by using excipients for example, white sugar, lactose, glucose, starch, mannitol, etc.; binding agents for example, syrup, gum arabi, tragacanth gum, sorbitol, methyl cellulose, polyvinyl pyrrolidone, etc.; disintegrating agents for example, starch, carboxymethyl cellulose and its calcium salt, microcrystalline cellulose, polyethylene glycols, etc.; lubricants for example, talc, magnesium stearate, calcium stearate, silica, etc.; wetting agents for example, sodium laurate, glycerol, etc.; by means of conventional methods.

In preparing injection preparations, and other liquid preparations such as emulsions, suspensions and syrup preparations, they can be prepared, by means of conventional methods and suitably using solvents for example, ethanol, isopropyl alcohol, propylene glycol, 1,3-butylene glycol, polyethylene glycols, castor oil and the like for dissolving the active ingredient; surface active agents for example fatty acid esters of sorbitol, fatty acid esters of polyoxyethylene sorbitol, esters of polyoxyethylene, polyoxyethylene ether of hydrogenated castor oil, lecithin and the like; suspending agents for example cellulose derivatives such as sodium carboxymethyl cellulose, methyl cellulose and the like, and natural gums such as gum tragacanth, gum arabi and the like; preservatives for example esters of paraoxybenzoic acid, benzalkonium chloride, sorbitan fatty acid salts and the like.

In preparing suppositories, they can be prepared by means of conventional methods and by using excipients such as polyethylene glycols, lanolin, coconut oil and the like.

Dosages of the desired pharmaceutical composition for treating and preventing hyperlipidemia according to the present invention may suitably be selected depending upon methods of administration, the form of the preparation, age of the patient, body weight of the patient, sensitivities of the patient, conditions of the disease, and other factors. Generally, the amount of the active ingredient to be contained in each of these pharmaceutical compositions may be within about 0.05 to 80 mg/kg, preferably about 0.1 to 50 mg/kg of the body weight per day.

The present invention will be explained in more detail by illustrating the following Examples, Pharmaceutical preparations and Pharmacological test results. However, the present invention are not restricted only to these disclosures.

phosphinoylmethy-N-(50methyl-3-isoxazolyl)benzamide as colorless needles. Melting point: 152°-152° C.

EXAMPLES 2-6

By procedure similar to that employed in Example 1, there were prepared compounds of Examples 2-6 as shown in Table 1, in which the compound prepared in Example 1 is also shown.

TABLE 1

| Example No. | R¹ | R² | R³ | X | Melting point (°C.) | Recrystallization solvent |
|---|---|---|---|---|---|---|
| 1 | (5-methyl-3-isoxazolyl) | H | —CH₂CH₃ | O | 151–152 | Benzene-n-hexane |
| 2 | (methoxycarbonyl-pyridyl) | H | —CH₂CH₃ | O | 167–169 | Benzene-n-hexane |
| 3 | (2,6-dibromo-3-pyridyl) | H | —CH₂CH₃ | O | 178.5–180.0 | Benzene-n-hexane |
| 4 | phenyl | phenyl-NH— | —CH₂CH₃ | O | 113–115 | Benzene-n-hexane |
| 5 | (indazolyl-NH—) | H | —CH₂CH₃ | O | 179–180 | Benzene-n-hexane |
| 6 | —H₂CH₂C—(phenylene)—CH₂— | | —CH₂CH₃ | O | Oily substance | *¹H-NMR spectrum data are shown below. |

*¹H-NMR spectrum data: (CDCl₃, Internal standard: TMS),
(δ value: ppm): 1.27 (t, J=7.0Hz, 6H), 2.7-3.1 (m, 2H), 3.19 (d, J=22.0Hz, 2H), 3.4–4.0 (m, 2H), 3.8–4.2 (m, 4H), 4.3–5.0 (m, 2H), 7.1–7.5 (m, 8H)

EXAMPLE 1

1.36 Grams (5 mM) of 4-diethoxyphosphinoylmethylbenzoic acid and 0.40 g (5 mM) of 3-amino-5-methylisoxazole were dissolved in 15 ml of dry N,N-dimethylformamide (DMF). To this solution was added dropwise 2 ml of dry DMF solution with 1.00 g (5.5 mM) of diethyl phosphorocyonidate, then was added dropwise 3 ml of dry DMF solution with 0.56 g (5.5 mM) of triethylamine for 5 minutes at 0° C. The resulting reaction mixture was stirred for 30 minutes at 0° C. and was further stirred for additional 1 hour at room temperature. To this reaction mixture was added 30 ml of water, and extracted with ethyl acetate. The ethyl acetate solution was washed with water, dried over anhydrous sodium sulfate, and concentrated. The residue was subjected to by means of a silica gel column chromatography (eluted with chloroform:ethyl acetate=1:1), then the crude crystals were recrystallized from benzene-n-hexane to yield 0.53 g of 4-diethoxy-

EXAMPLE 7

1.80 Grams (15 mM) of indoline, 1.82 g (18 mM) of triethylamine and 0.37 g (3 mM) of 4-dimethylaminopyridine were dissolved in 30 ml of dry dichloroethane, to this solution was added dropwise slowly 30 ml of dry dichloromethane solution with 5.21 g (15 mM) of 4-diethoxyphosphinoylmethylbenzoyl chloride at 0° C. with stirring. After the stirring was continued for 10 hours at room temperature, 50 ml of water was added to the reaction mixture and extracted with chloroform. The extracts were dried over anhydrous sodium sulfate, and concentrated. The residue thus obtained was purified by means of a silica gel column chromatography (eluted with chloroform:ethyl acetate=1:1). The crude crystals were recrystallized from benzene-n-hexane to yield 3.90 g of 1-(4-diethoxyphosphinoylmethylbenzoyl)indoline as colorless crystals Melting point 93.0°–94.5° C.

EXAMPLES 8–26

By procedure similar to that employed in Example 7, there were prepared compounds of Examples 8–26 as shown in Table 2. In Table 2, the compounds prepared by Examples 7 and 27 are also mentioned.

TABLE 2

$$\underset{R^2}{\overset{R^1}{}}N-\overset{\overset{X}{\|}}{C}-\underset{}{\bigcirc}-CH_2-\underset{\overset{\|}{O}}{P}(OR^3)_2$$

| Example No. | R¹ | R² | R³ | X | Melting point (°C.) | Recrystallization solvent |
|---|---|---|---|---|---|---|
| 7 | 2-methylphenyl-CH₂CH₂— | | —CH₂CH₃ | O | 93.0–94.5 | Benzene-n-hexane |
| 8 | (phenothiazinyl, Cl-substituted) | | —CH₂CH₃ | O | 133–135 | Benzene-n-hexane |
| 9 | 2-methylphenyl-CH₂CH₂CH₂— | | —CH₂CH₃ | O | 66–68 | Diethyl ether-n-hexane |
| 10 | 2-methylphenyl-OCH₂CH(phenyl)— | | —CH₂CH₃ | O | 168–170 | Benzene-n-hexane |
| 11 | (1-methylnaphthyl) | H | —CH₂CH₃ | O | 145.0–146.5 | Dichloromethane-diethyl ether |
| 12 | (5-bromo-2-methyl-phenyl with CONH₂) | H | —CH₂CH₃ | O | 168–170 | Chloroform-n-hexane |
| 13 | (5-bromo-2-methyl-phenyl with COCH₃) | H | —CH₂CH₃ | O | 121–122 | Benzene-n-hexane |
| 14 | (5-bromo-2-methyl-phenyl with COC₆H₅) | H | —CH₂CH₃ | O | 111.5–112.5 | Benzene-n-hexane |

TABLE 2-continued

Structure: R¹R²N-C(=X)-C₆H₄-CH₂-P(=O)(OR³)₂

| Example No. | R¹ | R² | R³ | X | Melting point (°C.) | Recrystallization solvent |
|---|---|---|---|---|---|---|
| 15 | 4-(H₃CCO)-3-Br-phenyl | H | —CH₂CH₃ | O | 153.5–154.5 | Benzene-n-hexane |
| 16 | 4-((H₃C)₂N)-phenyl | H | —CH₂CH₃ | O | 149–150 | Dichloromethane-diisopropyl ether |
| 17 | 4-(phenylthio)phenyl | H | —CH₂CH₃ | O | 140–142 | Benzene-n-hexane |
| 18 | 4-(H₃CS)-phenyl | H | —CH₂CH₃ | O | 150–153 | Benzene-n-hexane |
| 19 | 4-(H₂NO₂S)-phenyl | H | —CH₂CH₃ | O | 263–265 (decomposed) | Methanol |
| 20 | 4-benzoylphenyl | H | —CH₂CH₃ | O | 182–183.5 | Chloroform-n-hexane |
| 21 | 4-(H₃C-CO)-phenyl | H | —CH₂CH₃ | O | 182–183 | Chloroform-n-hexane |
| 22 | 4-Cl-2-(phenoxycarbonyl? see structure)-phenyl | H | —CH₂CH₃ | O | 112–114.5 | Benzene-n-hexane |
| 23 | 5-Cl-pyridin-2-yl | H | —CH₂CH₃ | O | 116–117 | Benzene-n-hexane |
| 24 | 5-Br-pyridin-2-yl | H | —CH₂CH₃ | O | 126.5–127.5 | Benzene-n-hexane |
| 25 | pyridin-4-yl | H | —CH₂CH₃ | O | 141–143 | Chloroform-n-hexane |

TABLE 2-continued

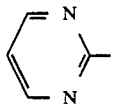

| Example No. | R¹ | R² | R³ | X | Melting point (°C.) | Recrystallization solvent |
|---|---|---|---|---|---|---|
| 26 | 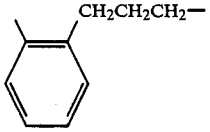 | H | —CH₂CH₃ | O | 125–127 | Benzene-n-hexane |
| 27 | 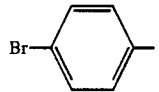 | | —CH₂CH₃ | S | 96–97 | Benzene-n-hexane |

EXAMPLE 27

0.77 Gram (2.0 mM) of 1-(4-diethoxyphosphinoylmethylbenzoyl)-1,2,3,4-tetrahydroquinoline and 1.0 g (4.6 mM) of phosphorus pentasulfide were suspended in a mixed solvent consisting of 20 ml of anhydrous benzene and 5 ml of anhydrous pyridine This suspension was heated and refluxed for 7 hours. After the reaction mixture was cooled to room temperature, the mixture was poured into 50 ml of ice-water, and the aqueous phase was acidified with 4N hydrochloric acid and then extracted with chloroform. The chloroform solution was dried over anhydrous sodium sulfate, and concentrated. Thus obtained residue was purified by means of a silica gel column chromatography (eluted with chloroform:ethyl acetate=1:1). The crude crystals were recrystallized from benzene-n-hexane to yield 0.23 g of 1-[(4-diethoxyphosphinoylmethylphenyl)thiocarbonyl]-1,2,3,4-tetrahydroquinoline as yellowish crystals. Melting point 96°–97° C.

EXAMPLES 28–54

By procedure similar to that employed in Example 7, there were prepared compounds of Examples 28–54 as shown in Table 3 as follows.

TABLE 3

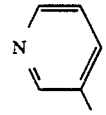

| Example No. | R¹ | R² | R³ | X | Melting point (°C.) | Recrystallization solvent |
|---|---|---|---|---|---|---|
| 28 | 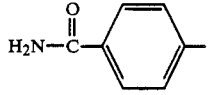 | H₅C₂—O—C(=O)—(CH₂)₃— | —CH₂CH₃ | O | Oily substance | **¹H-NMR spectrum data are shown below. |
| 29 | 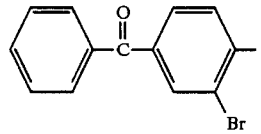 | H | —CH₂CH₃ | O | 162–164 | Chloroform-n-hexane |
| 30 | H₂N—C(=O)—⟨phenyl⟩— | H | —CH₂CH₃ | O | 223–225 | Chloroform-n-hexane |
| 31 | ⟨phenyl⟩—C(=O)—⟨phenyl-Br⟩— | H | —CH₂CH₃ | O | 108–109 | Benzene-n-hexane |

TABLE 3-continued $$\underset{R^2}{\overset{R^1}{\text{N}}}\!\!-\!\!\overset{X}{\underset{\|}{\text{C}}}\!\!-\!\!\!\left\langle\!\!\!\!\bigcirc\!\!\!\!\right\rangle\!\!-\!\!\text{CH}_2\!\!-\!\!\underset{\underset{\text{O}}{\|}}{\text{P}}(\text{OR}^3)_2$$

| Example No. | R¹ | R² | R³ | X | Melting point (°C.) | Recrystallization solvent |
|---|---|---|---|---|---|---|
| 32 | 2-bromo-5-(acetyl) phenyl | H | —CH₂CH₃ | O | 162–163 | Benzene-n-hexane |
| 33 | 6-methoxy-3-pyridyl | H | —CH₂CH₃ | O | 106–107 | Benzene-n-hexane |
| 34 | 2-benzoylphenyl | H | —CH₂CH₃ | O | 110–111 | Benzene-n-hexane |
| 35 | 4-bromo-1-naphthyl | H | —CH₂CH₃ | O | 172–173 | Benzene-n-hexane |
| 36 | 4-chloro-1-naphthyl | H | —CH₂CH₃ | O | 167–168 | Chloroform-n-hexane |
| 37 | 4-(methylsulfonyl)phenyl | H | —CH₂CH₃ | O | 178–179 | Chlorofrom-n-hexane |
| 38 | 5-chloro-2-(benzoyl)phenyl | CH₃ | —CH₂CH₃ | O | 135.5–136.5 | Benzene-n-hexane |
| 39 | 5-bromo-2-(N-benzylcarbamoyl)phenyl | H | —CH₂CH₃ | O | 136–139 | Benzene-n-hexane |

TABLE 3-continued

Structure: R¹R²N-C(=X)-C₆H₄-CH₂-P(=O)(OR³)₂

| Example No. | R¹ | R² | R³ | X | Melting point (°C.) | Recrystallization solvent |
|---|---|---|---|---|---|---|
| 40 | 5-bromo-2-methyl-N-(2-phenylethyl)benzamide group (-CONHCH₂CH₂-C₆H₅ with Br, CH₃ on ring) | H | —CH₂CH₃ | O | 159–160 | Chloroform-n-hexane |
| 41 | 4-(phenylsulfinyl)phenyl (C₆H₅-SO-C₆H₄-) | H | —CH₂CH₃ | O | 170–171 | Chloroform-n-hexane |
| 42 | 5-bromo-2-methyl-(n-butyl)phenyl | | —CH₂CH₃ | O | 85–86 | Diethyl ether-n-hexane |
| 43 | 3-chloro-4-methyl-(acetyl)phenyl (H₃C-CO- with Cl, CH₃) | H | —CH₂CH₃ | O | 124.5–126.5 | Benzene-n-hexane |
| 44 | 3-bromo-4-pyridyl | H | —CH₂CH₃ | O | 116.5–117.5 | Benzene-n-hexane |
| 45 | 5-bromo-2-methyl-N-(4-chlorophenyl)benzamide | H | —CH₂CH₃ | O | 219–221 | Chloroform-n-hexane |
| 46 | 5-chloro-2-methyl-N-(2-methoxyphenyl)benzamide | H | —CH₂CH₃ | O | Oily substance | ***NMR spectrum data are shown below |
| 47 | 5-chloro-2-methyl-[4-(phenyl)piperazin-1-yl]carbonyl phenyl | H | —CH₂CH₃ | O | Oily substance | ****NMR spectrum data are shown below |

TABLE 3-continued
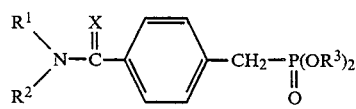
| Example No. | R[1] | R[2] | R[3] | X | Melting point (°C.) | Recrystallization solvent |
|---|---|---|---|---|---|---|
| 48 | 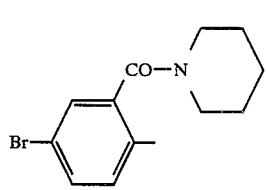 | H | —CH$_2$CH$_3$ | O | 166–168 | Benzene-n-hexane |
| 49 | 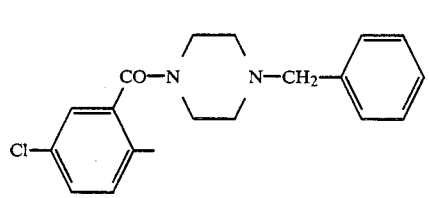 | H | —CH$_2$CH$_3$ | O | 134–135 | Benzene-n-hexane |
| 50 | 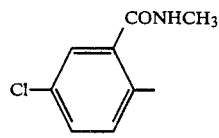 | H | —CH$_2$CH$_3$ | O | 166–167 | Chloroform-n-hexane |
| 51 | 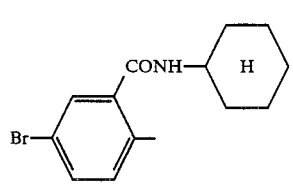 | H | —CH$_2$CH$_3$ | O | 202–204 | Chloroform-n-hexane |
| 52 | 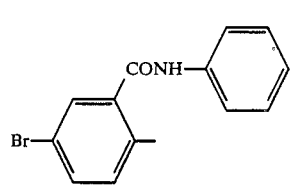 | H | —CH$_2$CH$_3$ | O | 191.5–193.3 | Chloroform-n-hexane |
| 53 | 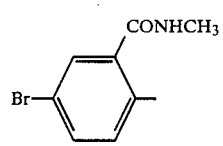 | H | —CH$_2$CH$_3$ | O | 170–171 | Chloroform-n-hexane |

TABLE 3-continued

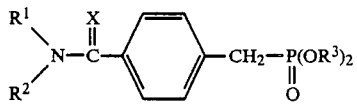

| Example No. | R¹ | R² | R³ | X | Melting point (°C.) | Recrystallization solvent |
|---|---|---|---|---|---|---|
| 54 | (Br-, CH3-substituted phenyl-CONH-phenyl group) | H | —CH₂CH₃ | O | 201–203 | Chloroform-n-hexane |

Note:
NMR spectrum Data
**Product of Example 28 (δ value: ppm)
1.18 (t, J=7.0Hz, 6H), 1.24 (t, J=7.5Hz, 3H), 1.8–2.0 (m, 2H), 2.37 (t, J=7.8Hz, 2H), 3.06 (t, J=22.0Hz, 2H), 3.8–4.0 (m, 6H). 4.11 (q, J=7.5Hz, 2H), 6.90 (d, J=8.2Hz, 2H), 7.1–7.4 (m, 6H)
***Product of Example 46 (δ value: ppm)
1.25 (t, J=7.0Hz, 6H), 3.22 (d, J=22.1Hz, 2H), 3.9–4.1 (m, 4H), 6.9–7.2 (m, 3H), 7.4–7.6 (m, 3H), 7.65 (d, J=2.5Hz, 1H), 7.97 (d, J=11.6Hz, 2H), 8.37 (d, J=7.9Hz, 1H), 8.5 (br. s, 1H), 8.82 (d, J=8.9Hz, 1H), 11.8 (br. s, 1H)
****Product of Example 47 (δ value: ppm)
1.26 (t, J=7.0Hz, 6H), 3.1–3.3 (m, 4H), 3.21 (d, J=22.0Hz, 2H), 3.6–4.0 (m, 4H), 3.9–4.1 (m, 4H), 6.9–7.5 (m, 9H), 7.87 (d, J=7.9Hz, 2H), 8.47 (d, J=8.9Hz, 1H), 9.96 (s, 1H)

Examples of Pharmaceutical Preparation - 1

Preparation of Tablets

Tablets (1,000 tablets) each of which containing 254 mg of 6-bromo-1-(4-diethoxyphosphinoylmethylbenzoyl)-1,2,3,4-tetrahydroquinoline (hereinafter referred to as "Compound A") as the active ingredient were prepared by the following formulation.

| Ingredients | Amount (g) |
|---|---|
| Compound A | 250 |
| Lactose (Japanese Pharmacopoeia grade) | 33.3 |
| Corn starch (Japanese Pharmacopoeia grade) | 16.4 |
| Calcium carboxylmethyl cellulose (Japanese Pharmacopoeia grade) | 12.8 |
| Mehtyl cellulose (Japanese Pharmacopoeia grade) | 6.0 |
| Magnesium stearate (Japanese Pharmacopoeia grade) | 1.5 |
| Total amount | 320 g |

In accordance with the above-mentioned formulation, Compound A, lactose, corn starch and calcium carboxymethyl cellulose were thoroughly admixed together, then the mixture was shaped into granular form by using an aqueous solution of methyl cellulose, then thus obtained granules were allowed to pass through a sieve (No. 24), the granules being passed through the sieve were mixed with magnesium stearate, then the thus obtained mixture was allowed to press into tablets form.

Example of Pharmaceutical Preparation - 2

Preparation of Capsules

Hard gelatin capsules (1,000 capsules) each of which containing 4-diethoxyphosphinoylmethyl-N-(2-benzoyl-4-bromophenyl)benzamide (hereinafter referred to as "Compound B") as the active ingredient were prepared by the following formulation.

| Ingredients | Amount (g) |
|---|---|
| Compound B | 250 |
| Crystalline cellulose (Japanese Pharmacopoeia grade) | 30 |
| Corn starch (Japanese Pharmacopoeia grade) | 17 |
| Talc (Japanese Pharmacopoeia grade) | 2 |
| Magnesium stearate (Japanese Pharmacopoeia grade) | 1 |
| Total amount | 300 g |

In accordance with the above-mentioned formulation, each of these ingredients was finely pulverized, then the pulverized ingredients were admixed thoroughly so as to have them a uniform mixture. The mixture was filled in a gelatin capsule for oral administration having the desired size to prepare capsule preparation.

Example of Pharmaceutical Preparation - 3

Preparation of Granules

Granules (1,000 g), containing 500 mg/g of 4-diethoxyphosphinoylmethyl-N-(4-acetyl-2-bromophenyl)benzamide (hereinafter referred to as "Compound C") as the active ingredient were prepared by the following formulation.

| Inqredients | Amount (g) |
|---|---|
| Compound C | 500 |
| Corn starch (Japanese Pharmacopoeia grade) | 250 |
| Lactose (Japanese Pharmacopoeia grade) | 100 |
| Crystalline cellulose (Japanese Pharmacopoeia grade) | 100 |
| Calcium carboxymethyl cellulose (Japanese Pharmacopoeia grade) | 40 |
| Hydroxypropyl cellulose (Japanese Pharmacopoeia grade) | 10 |
| Total amount | 1,000 g |

In accordance with the above-mentioned formulation, Compound C, corn starch, lactose, crystalline cellulose and calcium carboxymethyl cellulose were admixed thoroughly, then an aqueous solution of hydroxypropyl cellulose was added to the mixture and kneaded, then by using a extruding granulating machine to prepare granules, and dried them at 50° C. for 2 hours to prepare the desired granular preparation.

Pharmacological Tests

Increasing rate (%) of plasma high density lipoprotein cholesterol (HDLC) concentration in the serum, and decreasing rate (%) of plasma triglyceride (TG) concentration in the serum, each of which is performed by a carboxamide compound of the general formula (I) according to the present invention were conducted as follows.

Test Methods

Seven-week-old male Wistar rats were used.

The test compound was orally administered for two (2) days at a daily dose of 300 mg/kg body weight to each of six (6) rats in test group. The dosing vehicle was 0.5% sodium carboxymethylcellulose solution, and the dosing volume was 5 ml/kg body weight.

Similar to the procedures taken in the rats in the test group, to each one of six (6) rats in control group was orally administered 0.5% sodium carboxymethylcellulose solution only.

On day 2, after fasting for 20 hours, blood was drawn from the jagular sinus with a heparinized syringe. Plasma was obtained by centrifugation.

Plasma HDLC was determined after precipitation of other lipid fraction with heparin and $Ca^{2+}$ [HDL-C Kit-N, (manufactured by Nihon Shoji Kabushiki Kaisha)].

Plasma TG was determined by using a modification of method of Van Handel [Clin. Chem., 7, 241, (1961)], [Triglyceride G-Test Wako (manufactured by Wako Pure Chemical Co., Ltd.)].

Increasing rate (%) of plasma HDLC concentration was calculated from the formula as follows:

$$\text{Increasing rate (\%)} = \frac{\left[\text{Plasma } HDLC \text{ concentration of test group}\right]}{\left[\text{Plasma } HDLC \text{ concentration of control group}\right]} \times 100$$

Decreasing rate (%) of plasma TG concentration was calculated from the formula as follows:

$$\text{Decreasing rate (\%)} = \frac{\left[\text{Plasma } TG \text{ concentration of test group}\right]}{\left[\text{Plasma } TG \text{ concentration of control group}\right]} \times 100$$

Test Results

The test results are shown in Table 4 as follows:

TABLE 4

| Test Compound | Increasing rate (%) of plasma HDLC concentration | Decreasing rate (%) of plasma TG concentration |
|---|---|---|
| Compound of Example 13 | 222 | 83 |
| Compound of Example 14 | 267 | 48 |
| Compound of Example 15 | 235 | 79 |
| Compound of Example 20 | 206 | 66 |
| Compound of Example 21 | 332 | 61 |
| Compound of Example 22 | 207 | 60 |
| Compound of Example 24 | 168 | 60 |
| Compound of Example 25 | 222 | 59 |
| Compound of Example 33 | 148 | 65 |
| Compound of Example 42 | 171 | 85 |
| Compound of Example 43 | 271 | 67 |
| Compound of Example 50 | 184 | 79 |

What is claimed is:

1. A carboxamide compound represented by the general formula (I), $$R^1\underset{R^2}{\overset{}{\diagdown}}N-\overset{X}{\underset{\|}{C}}-\underset{}{\bigcirc}-CH_2-\underset{\underset{O}{\|}}{P(OR^3)_2} \quad (I)$$

wherein
$R^1$ and $R^2$ are each:
a hydrogen atom;
a lower alkyl group;
a phenyl group which may have 1 to 3 substituents selected from the group consisting of a halogen atom, a carbamoyl group, an N-(lower alkyl)carbamoyl group, an N-(cycloalkyl)carbamoyl group, an N-(phenyl)carbamoyl group which may have halogen atoms, lower alkoxy groups or lower alkyl groups as substituents on the phenyl ring, an N-(phenyl-lower alkyl)carbamoyl group, a lower akanoyl group, a benzoyl group, an N,N-di(lower alkyl)amino group, a phenylthio group, a lower alkylthio group, a lower alkylsulfinyl group, a phenylsulfinyl group, a 4-phenylpiperazinylcarbonyl group, a 4-(phenyl-lower alkyl)piperazinylcarbonyl group, a piperidinylcarbonyl group and a sulfamoyl group;
a lower alkoxycarbonyl-lower alkyl group;
a pyridyl group which may have 1 to 3 substituents selected from the group consisting of a halogen atom, a lower alkoxy group and a lower alkoxycarbonyl group;
an N-phenylamino group;
a naphthyl group which may have halogen atoms as substituents;
a pyrimidinyl group;
an isoxazolyl group which may have lower alkyl groups as substituents; or
an N-phthalazinylamino group;

further, $R^1$ and $R^2$ together with the adjacent nitrogen atom bonded thereto form a heterocyclic group consisting of an indolin-1-yl group, a 1,2,3,4-tetrahydroquinolin-1-yl group which may have halogen atoms as substituents, 1,2,3,4-tetrahydroisoquinolin-2-yl group, a 2,3-dihydro-4H-1,4-benzoxazin-4-yl group which may have a phenyl group at the 2- or 3-position in the benzoxazine ring, and a phenothiazin-10-yl group which may have halogen atoms as substituents in the benzene ring;

provided that, $R^1$ and $R^2$ are not hydrogen atoms at the same time; and when any one of $R^1$ and $R^2$ is a lower alkyl group, then the other is a phenyl group having a halogen atom and a benzoyl group as substituents; or when any one of $R^1$ and $R^2$ is a phenyl group having a halogen atom as a substituent, then the other is a lower alkoxycarbonyl-lower alkyl group; further, when any one of $R^1$ and $R^2$ is a phenyl group, then the other is an N-phenylamino group;

$R^3$ is a lower alkyl group; and

X is an oxygen atom or a sulfur atom.

2. The carboxamide compound represented by the general formula (I) as claimed in claim 1, wherein $R^1$ and $R^2$ are each:
   a hydrogen atom;
   a lower alkyl group;
   a phenyl group which may have 1 to 3 substituents selected from the group consisting of a halogen atom, an N-(lower alkyl)carbamoyl group, a lower alkanoyl group and a benzoyl group;
   further, $R^1$ and $R^2$ together with the adjacent nitrogen atom bonded thereto form an 1,2,3,4-tetrahydroquinolin-1-yl which may have halogen atoms as substituents;

provided that, $R^1$ and $R^2$ are not hydrogen atoms at the same time;

$R^3$ is a lower alkyl group; and

X is an oxygen atom or a sulfur atom.

3. The carboxamide compound represented by the general formula (I) as claimed in claim 1, wherein the carboxamide compound is selected from the group consisting of:
4-diethoxyphosphinoylmethyl-N-(4-benzoyl-2-bromophenyl)benzamide,
4-diethoxyphosphinoylmethyl-N-(4-chloro-2-benzoylphenyl)-N-methylbenzamide,
4-diethoxyphosphinoylmethyl-N-[4-chloro-2-(N-methylcarbamoyl)phenyl]benzamide,
4-diethoxyphosphinoylmethyl-N-[4-bromo-2-(N-methylcarbamoyl)phenyl]benzamide,
4-diethoxyphosphinoylmethyl-N-(4-acetyl-2-chlorophenyl)benzamide,
4-diethoxyphosphinoylmethyl-N-(4-bromo-2-oylphenyl)benzamide,
4-diethoxyphosphinolymethyl-N-(4-chloro-2-benzoylphneyl)benzamide, and
6-bromo 1-(4-diethoxyphosphinoylmethylbenzoyl)-1,2,3,4-tetrahydroquinoline.

4. A pharmaceutical composition for treating and/or preventing hyperlipidemia containing, as the active ingredient, a carboxamide compound represented by the general formula (I) as claimed in claim 1.

5. A method for treating and/or preventing hyperlipidemia by administering a pharmaceutical composition as claimed in claim 4 containing, as the active ingredient, a carboxamide compound represented by the general formula (I), at a dosage rate of 0.05 to 80 mg/kg body weight/day.

* * * * *